United States Patent [19]

Caślavský et al.

[11] 4,411,889

[45] Oct. 25, 1983

[54] SELF-GELLING LIQUID COMPOSITION FOR TOPICAL APPLICATION IN THE ORAL CAVITY

[75] Inventors: Véra B. Caślavský, Lexington; Poul Gron, Needham, both of Mass.; Howard Fine, Montreal, Canada

[73] Assignee: Forsyth Dental Infirmary for Children, Boston, Mass.

[21] Appl. No.: 381,530

[22] Filed: May 24, 1982

[51] Int. Cl.³ .................. A61K 7/18; A61K 33/16
[52] U.S. Cl. ........................................ 424/151; 424/52
[58] Field of Search ................................ 424/49–58, 424/151

[56] References Cited

U.S. PATENT DOCUMENTS

| | | | |
|---|---|---|---|
| 3,337,412 | 8/1967 | Elbreder | 424/151 |
| 4,143,126 | 3/1979 | Gaffar | 421/49 |
| 4,165,366 | 8/1979 | Mellberg | 424/49 |
| 4,165,368 | 8/1979 | Gaffar | 424/52 |
| 4,267,167 | 5/1981 | Weitzman et al. | 424/52 |
| 4,353,892 | 10/1982 | Caslavsky et al. | 424/52 |

FOREIGN PATENT DOCUMENTS 55-6385  2/1980  Japan.

OTHER PUBLICATIONS

Yu, et al. Chem. Abstr. 97#275427(1982) of Guisuanyan Xvebao(1981) 9(4):388–394.
Caslavska et al. Chem. Abstr. 96#155477s(1982) of Caries Res. (1982) 16(2):170-8
Gron et al. Chem. Abstr. 95#197136g(1981) of Caries Res. (1981) 15(6):453-461.
Rupprecht et al. Chem. Abstr. 94#127238e(1981) of Pharm. Ind. (1980) 42(12):1296-9.
Unger et al. Chem. Abstr. 94#127220x(1981) of Pharm. Ind. (1980)42(11):1130-4.
Gron et al. Chem. Abstr. 93#215258w(1980) of Caries Res. (1981) 15(1):90-7.
Institute Prod. Dev. Science Chem. Abstr. 93#210304y(1980) of Jpn. Tokkyokoho 80 06385 Feb. 15, 1980.
Klein et al. Chem. Abstr. 93#54708A(1980) of J. Non. Cryst. Solids(1980) (38–39)(1):45-50.
Caslavska et al. Chem. Abstr. 83#108076g(1975) of Arch. Oral Biol. (1975) 20(5/6):333-9.
Yoshida et al. Chem. Abstr. 81#5137g (1974) of Japan Kokai 73 93636, Dec. 04, 1973.
Caslavska et al. Chem. Abstr. 76#30670e(1972) of Arch Oral Biol (1971)16(10):1173-1180.
Rogovina et al. Chem. Abstr. 97#93317z(1982) of ZH. Khim. (1982) Abstr. #12576.
Brinker et al. Chem. Abstr. 97#77321r(1982) of J. Non-Cryst. Solids(1982)48(1):47-64.

*Primary Examiner*—Shep K. Rose
*Attorney, Agent, or Firm*—Richard P. Crowley

[57] ABSTRACT

A self-gelling composition for topical application, particularly in the oral cavity, which composition comprises: an aqueous solution of ethyl orthosilicate monomer or prepolymer; an active ingredient, such as a fluoride, or an antibiotic for sustained release in the area of topical application; and a gelation agent, to provide, on mixing of the composition, the in situ gelling of the composition within a predetermined time period after topical application, to provide the penetration properties of a low-viscosity solution with the sustained release of the active ingredient from the gel.

25 Claims, No Drawings

SELF-GELLING LIQUID COMPOSITION FOR TOPICAL APPLICATION IN THE ORAL CAVITY

BACKGROUND OF THE INVENTION

Fluoride-containing compositions, such as solutions or gels, have been known and have been employed for use in professional topical applications to teeth in the oral cavity. Such topical compositions have been employed since studies have indicated that, when fluoride penetrates into tooth enamel from a topical application, the tooth enamel becomes more caries-resistant. It has been demonstrated that ammonium fluoride has been shown to be an effective topical fluoride agent in vitro, as well as in vivo, with respect to the amount of fluoride that penetrates into the tooth enamel and which becomes firmly bound to the tooth enamel (see V. Caslavska, et al, Response of Human Enamel to Topical Application of Ammonium Fluoride, Archs. Oral Biology, Vol. 16, pp. 1173–1180, 1971, and Paul F. DePaola, High-Concentration Fluoride Preparations and Use for Preventing Caries, U.S. Pat. No. 4,078,053, issued Mar. 7, 1978).

Typical fluoride solutions and gels that are available for use in professional topical applications are set forth in Fluorides: An Update for Dental Practice, American Academy of Pedodontics, 1976. One such solution is a neutral pH 7 sodium fluoride solution. This solution is applied by a technique that calls for a preapplication pumice prophylaxis, interproximal flossing and drying of the tooth surface with compressed air. A solution of neutral 2% sodium fluoride is applied with cotton rolls and allowed to dry for 3 to 4 minutes. Four of these applications are necessary over a one-month period, which means that one-week intervals are usually the protocol. However, the prophylaxis technique is required only for the first of the four visits. This procedure is best used at ages three, seven, ten and thirteen, to coincide with the eruption of the deciduous teeth and the young permanent teeth.

Another solution used is a 1.23% acidulated orthophosphate-fluoride pH 3.2 preparation applied semiannually. Pumice prophylaxis, flossing and drying of the teeth are also required with this treatment. The solution is then applied with cotton applications for 4 minutes, making sure that the applicators remain continuously during the four-minute period. The solution is then allowed to dry. The patient is permitted to expectorate, but cannot eat, drink or rinse for at least 30 minutes post-application.

A third preparation is an acidulated phosphate fluoride (APF)-stannous fluoride combination solution which requires application of the APF for 2 minutes, followed by a two-minute application of a 0.5% stannous fluoride solution. A 10% stannous fluoride solution, applied to air-dried teeth for 15 to 30 seconds, is another possible alternative.

With respect to gels, a widely used preparation is an APF gel. The protocol for use is the same as that for the APF solution, except that the preparation is applied with cotton tips or via a tray as a gel.

The use of a fluoride-containing solution or a gel provides certain problems and benefits on topical application. The fluoride-containing solution, being less viscous than a gel, tends to enter more readily into the narrow spaces between the teeth and to penetrate more deeply into sulci in a given period of time than gel-type compositions. However, such fluoride-containing solutions, by being less viscous, tend to be washed away from the tooth surfaces and crevices much easier than gels. The employment of gels, with viscosity-increasing agents, provides for retention of the fluoride-containing gel on the enamel surfaces for longer periods of time than fluoride solutions. However, viscosity-increasing agents do not facilitate penetration of such gels into narrow enamel pores and, thus, may reduce the amount of fluoride uptake by the dental enamel, and, where the gel is very viscous, the longer it takes for the fluoride to be released from the gel preparation. Despite the long release time, the fact that the gel stays longer on the tooth surface allows more reaction time with the enamel, which often compensates for the slower release time of the fluoride. It has been reported that the clinical effectiveness of solutions and gels of the same compound is quite similar (see Brudevold, F., Naujoks, R., 1978, Caries-Preventive Fluoride Treatment of the Individual, Caries Res. 12 (supp. 1): 52-64, and Wei, S.H.Y., 1973, Fluoride Uptake by Enamel from Topical Solutions and Gels: an in vitro Study, J. Dent. Chil. 40: 299-302).

Thus, it would be desirable to provide for a composition, method and technique which would have the advantages of both fluoride-containing solutions and gels, without the disadvantages of either.

SUMMARY OF THE INVENTION

The invention relates to self-gelling compositions adapted, on topical applications, to convert from a low-viscosity liquid to a gel state in situ at a given, predetermined time, to provide for the sustained release of an active ingredient incorporated into the composition in situ, and to a method of applying such compositions.

In particular, the invention concerns a self-gelling, fluoride-containing compositions for use in the topical delivery of fluoride to the enamel of teeth and to the method of preventing dental caries by applying fluoride in a sustained-release manner through such topical application.

Also, the invention relates to a self-gelling antibiotic- or antibacterial-agent-containing composition for use in the oral cavity in the treatment of oral diseases, particularly periodontal disease, by the sustained release of the agents after topical application.

The gelable composition of the invention comprises a low-viscosity, aqueous solution adapted to be converted, after mixing and topical application, from a liquid solution to a gel state. The self-gelling composition comprises an ingredient which undergoes a reaction, such as hydrolysis, with the formation of nontoxic polymer which converts the solution into a gel state. A typical material would include a silica acid ester monomer or prepolymer which, on hydrolysis, forms silica polymer and an alkyl alcohol. The compositions also includes one or more active ingredients which are to be used at the site of topical application, and for which active ingredients sustained release is desired at the location from the silicate. The composition also includes one or more gelling agents, such as gel catalysts or silicate esters, to convert the monomer or prepolymer orthosilicate into a gel state in a predetermined time period. Typically, the gelling agents may comprise fluoride ions, ammonium ions and surface-active agents, or combinations thereof. In some instances, the gelling agent, such as the fluoride and ammonium ion, may also act as the active ingredient in the composition.

The self-gelling composition is suitable for use on mucous membranes and in the oral cavity, particularly for application if dental-caries-preventive agents are to be applied to the tooth surface or an active ingredient is to be applied for the treatment of periodontal disease. The self-gelling liquid composition, which readily enters cavities or spaces, may be applied topically to the tooth surface, periodontal pockets or other locations, where in situ gelation is desired for the sustained release of the active ingredients.

The composition and technique of the invention permit the advantage of a low-viscosity solution which more readily penetrates and enters into and fills the narrow spaces, for example, between the teeth or periodontal pockets and into narrow cavities, and permits the easy application of a liquid to the substrate, such as by the use of a topical applicator, spraying, injecting, coating, swabbing or other techniques. The composition provides the advantage of gelling in situ at a predetermined time, so that the newly formed gel state will conform to the space and location of topical application and not be rinsed or washed away easily. A further advantage is that, on conversion to the gel state, the active ingredient is slowly released; that is, there is sustained release of the incorporated active agent, to provide for improved delivery of the agent to the particular site of topical application. The composition and technique have significant advantages over currently available compositions which are solutions, gels or ointments, and which compositions do not change their viscosity after application and, therefore, incorporate both the advantages and disadvantages of the initial state of the composition. The self-gelling composition combines the initial easy and rapid distribution and penetration properties of a solution with the slow release and retention properties of a gel.

This invention is particularly concerned with a self-gelling composition for use in the oral cavity, wherein an active ingredient, such as a fluoride-containing compound, is used. The use of a low-viscosity liquid composition allows greater penetration into deep sulci in a given period of time on topical application. On conversion to the gel state, the active fluoride has a reduced tendency to wash away from the tooth surface and the pockets and, therefore, would have a prolonged or sustained reaction time with the enamel, enabling the enamel to take up more of the fluoride.

The invention also concerns a self-gelling composition containing antibacterial agents, such as antibiotics, alone or in combination with fluoride and ammonium-containing compounds, for use in the oral cavity and on mucous membranes. These compositions permit the penetration of the agent into periodontal pockets and the retention and slow release of the agents in the pockets, after conversion to the gel state.

The silicic acid compounds useful in the practice of the invention include those ortho silicate monomers and prepolymers which hydrolyze to form a corresponding alkyl alcohol and an $SiO_2$, and include the tetraethyl ester of silica acid which, on hydrolysis and gelation, provides for the release of ethanol, a nontoxic compound. Other lower alkyl esters of ortho silicate may be employed, such as methyl or propyl esters; however, these compounds may be employed only where the corresponding by-products are acceptable for use, so the preferred compound is the tetraethyl ortho silicate monomer or prepolymer. The amount of the silicate in the composition may vary, but typically comprises up to about 50% by weight; for example, from about 5% to 30% by weight, and more particularly 10% to 25% by weight. The ortho silicate may be prepolymerized partly, in order to decrease the gelation time when topically applied, such as, for example, up to 50% prepolymerization, provided that the resulting composition is still of sufficiently low viscosity, so that the solution may be applied topically as a liquid prior to gelation.

In the preparation of a self-gelling composition suitable for use in the oral cavity, the active ingredient may be one or more water-soluble, fluoride-containing compounds, and more particularly preferred are ammonium fluoride compounds, although other compounds, such as sodium, potassium, fluoride, alone or in combination with ammonium fluoride and other suitable fluoride compounds, or in combination with other reagents, such as phosphates or monofluorophosphates, may be employed. Typically, the amount of the fluoride compound is sufficient to prevent or to inhibit dental caries, and more particularly usually ranges from 0.01 moles to 1.5 moles; for example, 0.5 to 1.2 moles. Where the active ingredient comprises a drug, such an an antibacterial agent like chlorhexidine, or an antibiotic like tetracycline or erythromycin, the amount of the drug is sufficient to prevent infection or to treat the condition for which it is applied and for the time period desired, such as an amount of 0.05% to 20% by weight; for example, 0.1% to 5%.

A gelling agent is employed to control gelling time. In order to provide working time for the application of the preparation, the apparent gelation; that is, conversion to the gel state, should be initiated at a certain time after the reaction has been started. The gelling time should be less than 24 hours and more typically, for the self-gelling composition, less than about 1 hour after application; for example, 30 minutes, and preferably less than about 15 minutes after application. The gelation should be completed substantially within a desired, predetermined gel time, such as about 5 minutes, and preferably less than 1 minute.

The amount and nature of the gelling agent are selected to provide the desired gelation time, and may vary, depending on the materials and amounts used. Typically, and, for example, where surface-active agents are used as the gelling agent, the amount may range from 0.01% to 5% by weight; for example, 0.1% to 2%. The gelling agent may comprise a fluoride ion, an ammonium ion or a surface-active agent, alone or in combination. Thus, in self-gelling, dental-caries-preventing compositions, the ammonium fluoride may serve as an active ingredient and as the gelling agent. Where a fluoride compound and a separate ammonium compound are used, the concentration of the ammonium compound may range in the same or similar concentration as the fluoride compound.

Surface-active agents may be used alone or with other gelling agents, and such surface-active agents would include, but not be limited to: pyridinium compounds, such as cetyl pyridinium bromide and chloride; alkali and ammonium salts of fatty-acid sulfates, such as the sodium salts of lauryl sulfate; and nonionic surface-active agents, such as the polyoxyethylene derivatives of fatty-acid partial esters of sorbitol anhydrides known as Tween surfactants (a trademark of ICI United States, Inc.), or combinations thereof.

A variety of buffering agents may be employed in the composition to provide a buffered pH, which include, but are not limited to, the weak acid salts, such as acetates, tartarates, such as the water-soluble salts of phosphoric acid, citric acid, tartaric acid, lactic acid, acetic acid and the like. These agents are employed in minor amounts; for example, 0.1% to 4% by weight of the composition, to provide a buffer and to maintain the pH of the composition. Typically, the pH of the aqueous solution may range from about pH 3 to as high as pH 8.5, but more typically ranges from about pH 4 to 7.5.

Other additive ingredients may be incorporated into the composition, such as viscosity-thickening and control agents, oils, flavoring and sweetening agents, coloring agents, stabilizers, solid particulate filler and inert materials, humectants, glycols and the like.

In use, the ingredients of the composition are combined by a vigorous mixing action, typically with a mechanical mixer just prior to use, by the applicator, such as a dentist or hygienist. Typically, a solution containing the active ingredients, such as a fluoride, and the gelling ingredient, such as a silicate monomer or polymer, is admixed with a solution containing the gelling agent. After mixing, the resulting low-viscosity solution is topically applied usually at least several minutes before the gel time, so that the liquid will be distributed and will penetrate the desired area prior to gelling. The gel time is that time after mixing of the ingredients and refers to the time at which the solution forms into a substantially semirigid gel phase or state.

The invention will be described for the purpose of illustration only in connection with particular examples; however, it is recognized that various changes, modifications and improvements may be made by those persons skilled in the art, all falling within the spirit and scope of the invention.

DESCRIPTION OF THE EMBODIMENTS

Self-gelling compositions were prepared by vigorous mechanical mixing of the following compositions, and the gel times of the compositions to change from a liquid to a gel state were noted.

EXAMPLE 1.

| | |
|---|---|
| 80 parts | 0.6 M sodium fluoride solution, pH 7 (neutral) |
| 20 parts | tetraethoxy silane (also known as tetraethyl orthosilicate) |
| 1 part | cetyl pyridinium chloride (surface-active agent) | gels in 1 minute and 50 seconds

EXAMPLE 2.

| | |
|---|---|
| 60 parts | 0.06 M sodium fluoride solution, pH 7 (neutral) |
| 40 parts | tetraethoxy silane (= tetraethyl orthosilicate) |
| 1 part | cetyl pyridinium chloride (surface-active agent) | gels in 8 minutes

Example 3.

| | |
|---|---|
| 80 parts | 0.5 M ammonium fluoride solution, pH 7 (neutral) |
| 20 parts | tetraethoxy silane (= tetraethyl orthosilicate) | gels in 20 minutes

EXAMPLE 4.

| | |
|---|---|
| 80 parts | 0.8 M ammonium fluoride solution, pH 7 (neutral) |
| 20 parts | tetraethoxy silane (= tetraethyl orthosilicate) | gels in 10 minutes

EXAMPLE 5.

| | |
|---|---|
| 80 parts | 1.5 M ammonium fluoride solution, pH 7 (neutral) |
| 20 parts | tetraethoxy silane (= tetraethyl orthosilicate) | gels in 6 minutes

EXAMPLE 6.

| | |
|---|---|
| 80 parts | 1.5 M ammonium fluoride, 1.5 M ammonium phosphate (buffer), pH 7 |
| 20 parts | tetraethoxy silane (= tetraethyl orthosilicate) |
| 1 part | sodium lauryl sulfate (surface-active agent) | gels in 3 minutes

EXAMPLE 7.

The same of Example 6, but with 0.01 part sodium lauryl sulfate.

gels in 6 minutes.

EXAMPLE 8.

| | |
|---|---|
| 80 parts | 0.8 M ammonium fluoride solution, pH 4.5 |
| 20 parts | tetraethoxy silane (= tetraethyl orthosilicate) | gels in 14 minutes

EXAMPLE 9.

| | |
|---|---|
| 80 parts | 0.8 M ammonium fluoride, 0.15 ammonium phosphate solution, pH 7 (neutral) |
| 20 parts | tetraethoxy silane (= tetraethyl orthosilicate) | gels in 8 minutes

EXAMPLE 10.

| | |
|---|---|
| 70 parts | 0.7 M sodium fluoride solution, pH 7 (neutral) |
| 20 parts | tetraethoxy silane (= tetraethyl orthosilicate) |
| 10 parts | aminopropyl triethoxy silane (= aminopropyl, triethyl orthosilicate) |
| 1 part | Tween 20 (surface-active agent) | gels in 9 minutes

EXAMPLE 11.

The same as Example 10, but, instead of Tween 20, 1 part of sodium lauryl sulfate was used.
gels in 7 minutes.

EXAMPLE 12.

| 70 parts | water |
|---|---|
| 20 parts | tetraethoxy silane (= tetraethyl orthosilicate) |
| 10 parts | aminopropyl triethoxy silane (= aminopropyl, triethyl orthosilicate) |
| 1 part | sodium lauryl sulfate (surface-active agent) |
| 0.2 parts | chlorohexidine (antibacterial agent) | gels in 5 minutes

EXAMPLE 13.

| 70 parts | water |
|---|---|
| 20 parts | tetraethoxy silane (= tetraethyl orthosilicate) |
| 10 parts | aminopropyl triethoxy silane (= aminopropyl, triethyl orthosilicate) |
| 1 part | sodium lauryl sulfate |
| 16 parts | erythromycin (antibiotic) | gels in 2 minutes

EXAMPLE 14.

| 60 parts | 0.1 M ammonium dihydrogen phosphate solution |
|---|---|
| 20 parts | tetraethoxy silane (= tetraethyl orthosilicate) |
| 20 parts | aminopropyl triethoxy silane (= aminopropyl, triethyl orthosilicate) |
| 0.1 parts | Tween 20 (surface-active agent) |
| 3.3 parts | tetracyclin (antibiotic) | gels in 2 minutes

Examples 1-11 are suitable for use in treating or preventing dental caries by the topical application of the aqueous solution to tooth surfaces, to provide for the sustained release of the fluoride from the gel into the tooth enamel.

Example 12 is a self-gelling composition having an antibacterial agent suitable for veterinary use, such as the treatment of mastitis, by the application or coating of the affected area with the liquid and the sustained release from the gel of the antibacterial agent.

Examples 13 and 14 are suitable for use in the treatment of diseases of the oral cavity, particularly periodontal disease, by the topical application of the solution to periodontal pockets and areas, to provide for the sustained release of the antibiotic agent.

What is claimed is:

1. A fluoride-containing, self-gelling aqueous composition for topical application on tooth surfaces in the oral cavity for the prevention of dental caries, which composition comprises in combination:

(a) a low-viscosity, liquid, aqueous solution of a monomer or prepolymer ethyl orthosilicate in an amount to provide for the conversion of the liquid to a gel state;

(b) a water-soluble fluoride compound in an amount to inhibit or prevent dental caries on topical application of the composition; and (c) a gelation agent in an amount to provide in situ self-gelation of the composition from a low-viscosity liquid composition to a gel state, on topical application of the liquid composition onto the surface of the teeth in a patient, the gelation from a liquid to a gel state occurring in a time period of about 1 hour or less after mixing by hydrolysis of the silicate.

2. The composition of claim 1 wherein the amount of the ethyl orthosilicate in the composition ranges from about 5% to 30% by weight.

3. The composition of claim 1 wherein the water-soluble fluoride is selected from the group consisting of sodium fluoride, potassium fluoride, ammonium fluoride and combinations thereof.

4. The composition of claim 1 wherein the water-soluble fluoride is present in an amount of from about 0.01 M to 1.5 M.

5. The composition of claim 1 wherein the gelation agent comprises from about 0.01% to 2% by weight of a surface-active agent.

6. The composition of claim 5 wherein the surface-active agent is selected from the group consisting of a sodium lauryl sulfate, a cetyl pyridinium halide, a nonionic polyoxyethylene derivative of fatty-acid partial esters of sorbitol anhydrides and combinations thereof.

7. The combination of claim 1 wherein the composition includes a buffering agent in an amount to provide for buffering of the pH of the solution from about 4.0 to 7.5.

8. The composition of claim 1 wherein the time from in situ gelation from a liquid to a gel state is about 10 minutes or less after admixing.

9. The composition of claim 1 which includes the addition of a viscosity-increasing agent in an amount of from about 0.01% to 1% by weight.

10. The composition of claim 1 wherein the monomer ethyl orthosilicate has been prepolymerized in an amount of up to 50%.

11. A self-gelling, fluoride-containing aqueous liquid composition for topical application and use on tooth surfaces in the oral cavity, which composition comprises:

(a) a solution of an ethyl orthosilicate, which solution contains from about 5% to 30% by weight of the ethyl orthosilicate;

(b) a water-soluble fluoride compound in an amount of from about 0.05 M to about 1.5 M;

(c) a surface-active gelling agent in an amount of from about 0.01% to 2% of the composition; and (d) the composition characterized by being a low-viscosity aqueous liquid solution having a pH of from about 3 to 8.5 which, after mixing and on topical application of the liquid onto the surface of the teeth in the oral cavity of a patient, gels in situ to a gel state in a time period of from about 1 hour or less, thereby providing a solution which more readily will enter into the narrow spaces between the teeth and into conformity with the teeth surface and forming a gel state, to provide for the sustained release of the fluoride into the enamel of the teeth.

12. The composition of claim 11 wherein the water-soluble fluoride is selected from the group consisting of sodium fluoride, potassium fluoride, ammonium fluoride and combinations thereof.

13. A method of preventing of inhibiting dental caries by the application of a fluoride-containing composition to teeth in the oral cavity, which method comprises:
   (a) topically applying to the surface of the teeth, or the mucous membranes in the oral cavity of a patient, a fluoride-containing, self-gelling composition, which composition comprises a low-viscosity, liquid, aqueous solution which includes an ethyl orthosilicate, a water-soluble fluoride and a gelling agent;
   (b) coating the teeth surfaces with the low-viscosity liquid composition on topical application and permitting the composition to enter into the narrow spaces between the teeth; and
   (c) converting the solution in situ from a liquid to a gel state within 1 hour of such topical application in the oral cavity, to provide a gel composition which conforms to and is retained on the teeth surfaces, to provide for the sustained release of the fluoride into the enamel of the teeth, thereby inhibiting or preventing dental caries.

14. The method of claim 13 wherein the ethyl orthosilicate comprises a tetraethyl orthosilicate monomer or prepolymer.

15. The method of claim 13 which includes vigorously admixing an aqueous solution containing the ethyl silicate and the water-soluble fluoride with a solution of the gelling agent.

16. The method of claim 13 wherein the gelling agent is selected from the group consisting of fluoride ions, ammonium ions, surface-active agents and combinations thereof in a sufficient amount, to provide, after mixing of the ingredients, the in situ conversion of the aqueous composition from a liquid to a substantially gel state in a time period of about 1 hour or less by hydrolysis of the silicate.

17. The method of claim 13 which includes employing in the self-gelling composition an aqueous neutral solution of a water-soluble fluoride.

18. The method of claim 13 wherein the self-gelling composition has a pH of from about 3 to 8.5.

19. A self-gelling aqueous composition for topical application in the oral cavity as a low-viscosity liquid and for sustained release of an active ingredient from a gel formed in situ in the oral cavity after application of the liquid, which aqueous composition comprises the following ingredients in combination:
   (a) a monomer or prepolymer hydrolyzable, alkyl orthosilicate in an amount to provide for the conversion of the liquid to a gel state;
   (b) an active ingredient comprising a water-soluble fluoride compound in an amount to inhibit dental caries; and
   (c) a gelling agent selected from the group consisting of fluoride ions, ammonium ions, surface-active agents and combinations thereof in a sufficient amount, to provide, after mixing of the ingredients, the in situ conversion of the aqueous composition from a liquid to a substantially gel state in a time period of about 1 hour or less by hydrolysis of the silicate.

20. The composition of claim 19 having a pH range of from about 3 to 8.5.

21. The composition of claim 19 wherein the silicate is selected from the group consisting of a tetraethyl orthosilicate, an aminopropyl triethyl orthosilicate and combinations thereof.

22. The composition of claim 19 wherein the water-soluble fluoride compound comprises ammonium fluoride.

23. The composition of claim 19 wherein the surface-active agent is selected from the group consisting of cetyl pyridinium halide, sodium lauryl sulfate, a nonionic polyoxyethylene derivative of fatty-acid partial esters of sorbitol anhydrides and combinations thereof.

24. The composition of claim 19 wherein the composition has a gel time of about 10 minutes or less.

25. The composition of claim 19 which includes ammonium phosphate.

* * * * *